United States Patent
Tsukamoto et al.

(10) Patent No.: US 12,357,842 B2
(45) Date of Patent: Jul. 15, 2025

(54) LIGHT IRRADIATION DEVICE AND LIGHT IRRADIATION SYSTEM

(71) Applicant: ILLUMI MEDICAL INC., Owariasahi (JP)

(72) Inventors: Toshihiko Tsukamoto, Owariasahi (JP); Kazuhide Sato, Owariasahi (JP)

(73) Assignee: ILLUMI MEDICAL INC., Owariasahi (JP)

( * ) Notice: Subject to any disclaimer, the term of this patent is extended or adjusted under 35 U.S.C. 154(b) by 0 days.

(21) Appl. No.: 18/966,106

(22) Filed: Dec. 2, 2024

(65) Prior Publication Data
US 2025/0090861 A1 Mar. 20, 2025

Related U.S. Application Data

(63) Continuation of application No. PCT/JP2023/008008, filed on Mar. 3, 2023.

(51) Int. Cl.
*A61N 5/06* (2006.01)
*A61N 5/067* (2006.01)

(52) U.S. Cl.
CPC ............ *A61N 5/062* (2013.01); *A61N 5/0603* (2013.01); *A61N 5/067* (2021.08); *A61N 2005/0602* (2013.01); *A61N 2005/063* (2013.01); *A61N 2005/0643* (2013.01)

(58) Field of Classification Search
CPC ...... A61N 5/062; A61N 5/0603; A61N 5/067; A61N 2005/0602; A61N 2005/063; A61N 2005/0643
See application file for complete search history.

(56) References Cited

U.S. PATENT DOCUMENTS

| | | |
|---|---|---|
| 6,814,698 B2 | 11/2004 | Barthel et al. |
| 2001/0055462 A1 | 12/2001 | Seibel |
| 2006/0161055 A1 | 7/2006 | Pewzner et al. |
| 2006/0212099 A1 | 9/2006 | Riddell |
| 2008/0009749 A1 | 1/2008 | Delianides et al. |
| 2009/0287197 A1 | 11/2009 | Hanley et al. |
| 2017/0246472 A1 | 8/2017 | Chen et al. |

(Continued)

FOREIGN PATENT DOCUMENTS

| | | |
|---|---|---|
| JP | H0751285 A | 2/1995 |
| JP | 2014104138 A | 6/2014 |
| JP | 2014523907 A | 9/2014 |

(Continued)

OTHER PUBLICATIONS

European Search Report dated May 7, 2025, in EP Application No. 23926163 (PCT Application No. PCT/JP2023008008), 12 pgs.

*Primary Examiner* — Gary Jackson
*Assistant Examiner* — Sebastian X Lukjan
(74) *Attorney, Agent, or Firm* — Best Mode IP Law, PLLC; Yusuke Hirai

(57) ABSTRACT

A light irradiation device is a light irradiation device for medical use having an elongated shape. The light irradiation device includes an optical fiber that transmits light emitted by a light source to a tip portion of the optical fiber. The tip portion of the optical fiber is formed in a bent portion that is bent with respect to an axial direction of a base portion to which the tip portion is connected. The light irradiation device emits light in a direction intersecting the axial direction of the base portion by emitting the light from a tip end of the bent portion in the optical fiber.

19 Claims, 8 Drawing Sheets

(56) References Cited

U.S. PATENT DOCUMENTS

2018/0154155 A1 6/2018 Keaveney et al.
2022/0229282 A1 7/2022 Katsurada et al.

FOREIGN PATENT DOCUMENTS

| JP | 2018000867 A | 1/2018 |
| JP | 2022-075134 | 5/2022 |
| WO | WO2020230517 A1 | 11/2020 |
| WO | WO2021039323 A1 | 3/2021 |
| WO | WO2021075141 A1 | 4/2021 |

LIGHT IRRADIATION DEVICE AND LIGHT IRRADIATION SYSTEM

CROSS REFERENCE TO RELATED APPLICATION

This application is a continuation application of International Patent Application No. PCT/JP2023/008008 filed on Mar. 3, 2023, which designated the U.S. The entire disclosure of the above application is incorporated herein by reference.

TECHNICAL FIELD

The present disclosure relates to a light irradiation device and a light irradiation system used inside a biological lumen to emit light.

BACKGROUND

PDT (Photodynamic Therapy) is known as one technique for treating diseases. In PDT, after a light-sensitive substance was administered into a living body, the living body is irradiated with light. As a result, cancer cells may be killed due to active oxygen generated in the cancer cells. However, in PDT, it is difficult to selectively have the light-sensitive substance absorbed only into cancer cells. Occurrence of side effects due to the photosensitive substance absorbed into normal cells is an issue with PDT.

In response to the issue, NIR-PIT (Near-Infrared Photoimmunotherapy) has been proposed in recent years. In NIR-PIT, a complex combining two compounds, an antibody against an antigen specific to cancer cells and a light-sensitive substance, is used. When administered into a living body, the complex is easily selectively accumulated only into cancer cells in the living body. Thereafter, the complex is activated by irradiating the living body with light having the excitation wavelength (e.g., wavelength including 690 nm, etc.) for the light-sensitive substance in the complex. In NIR-PIT, if the complex is selectively accumulated in cancer cells by antibodies and the cancer cells are locally irradiated with light, side effects are less likely to occur as compared to PDT.

The wavelength range including 690 nm is also called as a "spectroscopic window" of living bodies. The light within the range is less absorbed into the living body as compared to another wavelength range. On the other hand, light in the wavelength range including 690 nm is difficult to penetrate into a living body when the living body is irradiated from the body surface. Thus, it is difficult to treat a cancer existing deeply inside a living body by irradiation the living body with light from the body surface.

In view of this, instead of irradiating a living body with light from the body surface, a technology for irradiating a living body with light at a position closer to cancer cells has been proposed. For example, a light irradiation device described transmits light emitted from an external light source to a tip end of the light irradiation device via an optical fiber, and then emits the light in one direction from a side surface.

SUMMARY

A light irradiation device in a typical embodiment of the present disclosure is a light irradiation device for medical use that has an elongated shape and is configured to emit light from a most distal end after the light irradiation device was inserted into a lumen of a living body. The light irradiation device includes: an optical fiber that is configured to transmit light emitted by a light source to a tip portion of the optical fiber. The tip portion of the optical fiber is formed in a bent portion that is bent with respect to an axial direction of a base portion to which the tip portion is connected. A most distal end of the bent portion has a cut surface facing in a tip direction to serve as a most distal end surface of the light irradiation device from which light is emitted. Light having exited the most distal end surface is emitted in the tip direction of the bent portion to an outside of the light irradiation device by emitting the light from the most distal end surface of the bent portion in the optical fiber. The tip direction is a direction intersecting the axial direction of the base portion. The optical fiber includes a stiffening portion in at least a portion of an area where the bent portion is located. The stiffening portion is fixed to the bent portion of the optical fiber while allowing the light to be emitted in the tip direction from the most distal end surface of the bent portion. An angle of the bent portion with respect to the axial direction of the base portion of the optical fiber is stabilized by increasing a stiffness of the area in the optical fiber where the stiffening portion is disposed as compared to the optical fiber without the stiffening portion.

A light irradiation system in a typical embodiment of the present disclosure is a light irradiation system for medical use that is used after the light irradiation system was inserted into a lumen of a living body. The light irradiation system includes: a catheter that is formed in an elongated tubular shape; and a light irradiation device that is formed in an elongated shape, the light irradiation device being inserted into a lumen of the catheter and having a most distal end from which light is emitted. The light irradiation device includes an optical fiber that transmits light emitted by a light source to a tip portion of the optical fiber. The tip portion of the optical fiber is formed in a bent portion that is bent with respect to an axial direction of a base portion to which the tip portion is connected. A most distal end of the bent portion has a cut surface facing a tip direction to serve as a most distal end surface of the light irradiation device from which light is emitted. Light having exited the most distal end surface is emitted in the tip direction of the bent portion to an outside of the light irradiation device by emitting the light from the most distal end surface of the bent portion in the optical fiber. The tip direction is a direction intersecting the axial direction of the base portion. The optical fiber includes a stiffening portion in at least a portion of an area where the bent portion is located. The stiffening portion is fixed to the bent portion of the optical fiber while allowing the light to be emitted in the tip direction from the most distal end surface of the bent portion. An angle of the bent portion with respect to the axial direction of the base portion of the optical fiber is stabilized by increasing a stiffness of the area in the optical fiber where the stiffening portion is disposed as compared to the optical fiber without the stiffening portion.

DESCRIPTION OF EMBODIMENTS

Figure 1:
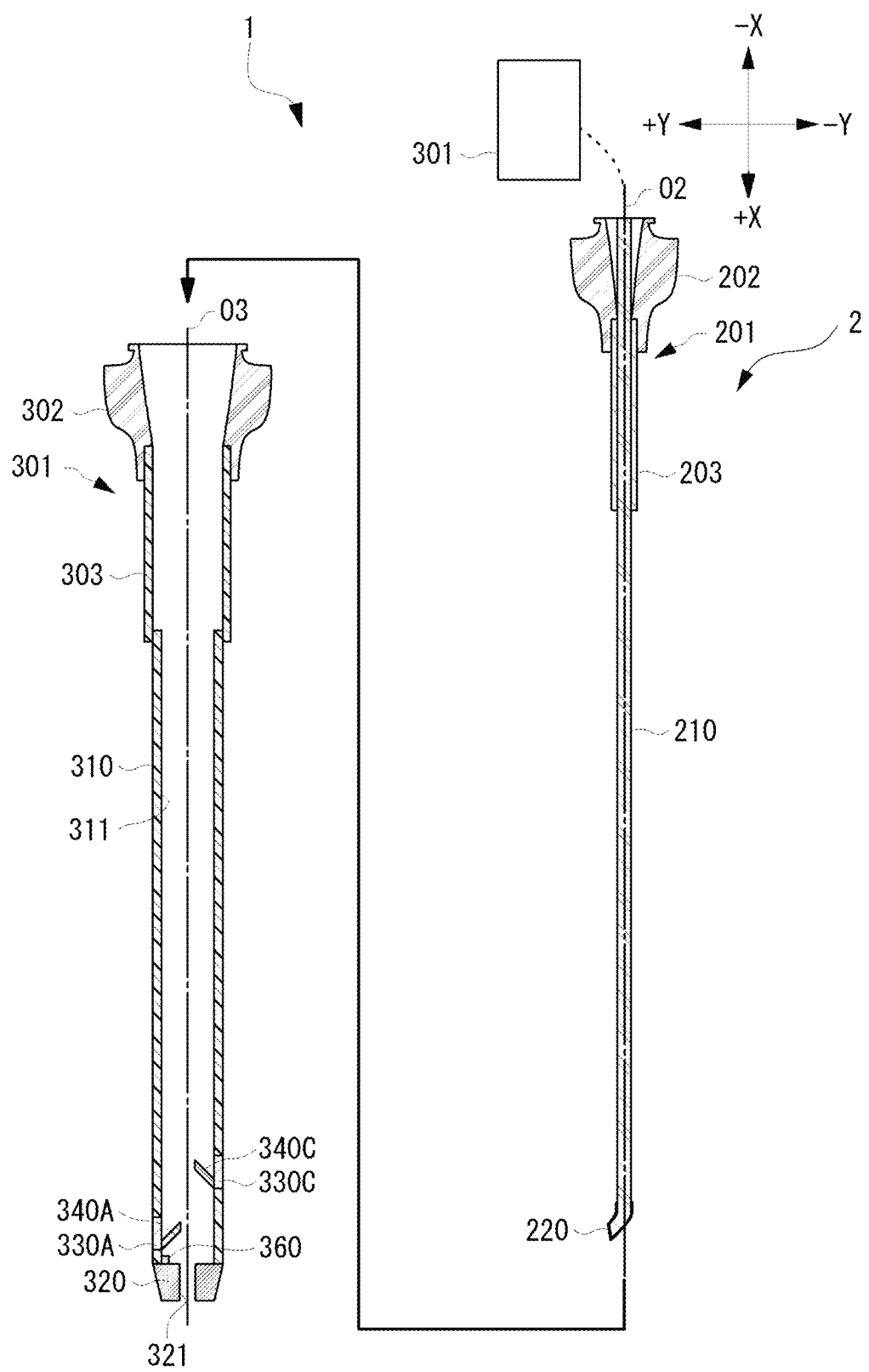
FIG. 1 is a longitudinal cross-sectional view of a light irradiation system 1 where a light irradiation device 2 and a catheter 3 are separated from each other.

Next, a relevant technology will be described below only for understanding the following embodiments. In a light irradiation device, the axial direction of the optical fiber that transmits the light emitted from the light source is aligned with the axial direction of the light irradiation device up to the tip portion of the device. In other words, the axial direction of the tip portion of the optical fiber is in parallel with the axial direction of the light irradiation device. Therefore, in the light irradiation device, in order to emit light in a direction intersecting the axial direction (i.e., a lateral direction), it is necessary to provide (i) a resin body that connects between the core of the optical fiber and a part of the side of the light irradiation device or (ii) a mirror that change the travel direction of the light emitted in a direction along the axis to a lateral direction. As a result, the structure of the tip portion of the light irradiation device may be complicated. Furthermore, when light passes through a resin body or the like, the light is more likely to lose energy. Therefore, it was difficult for conventional light emitting devices to efficiently emit light in a direction intersecting the axial direction with a simple configuration.

A typical objective of the present disclosure is to provide a light irradiation device and a light irradiation system that have a simple structure and are capable of efficiently emitting light in a direction intersecting the axial direction of an elongated main body.

A light irradiation device in a typical embodiment of the present disclosure is a light irradiation device for medical use that has an elongated shape and is configured to emit light from a most distal end, the light irradiation device including: an optical fiber that is configured to transmit light emitted by a light source to a tip portion of the optical fiber. The tip portion of the optical fiber is formed in a bent portion that is bent with respect to an axial direction of a base portion to which the tip portion is connected. A most distal end of the bent portion serves as the most distal end of the light irradiation device from which light is emitted. Light is emitted in a direction intersecting the axial direction by emitting the light from the most distal end of the bent portion in the optical fiber.

A light irradiation system in a typical embodiment of the present disclosure is a light irradiation system for medical use, including: a catheter that is formed in an elongated tubular shape; and a light irradiation device that is formed in an elongated shape, the light irradiation device being inserted into a lumen of the catheter and having a most distal end from which light is emitted. The light irradiation device includes an optical fiber that transmits light emitted by a light source to a tip portion of the optical fiber. The tip portion of the optical fiber is formed in a bent portion that is bent with respect to an axial direction of a base portion to which the tip portion is connected. A most distal end of the bent portion serves as the most distal end of the light irradiation device from which light is emitted. Light is emitted in a direction intersecting the axial direction of the base portion by emitting the light from the most distal end of the bent portion in the optical fiber.

According to the light irradiation device and the light irradiation system in the present disclosure, light is efficiently emitted in a direction intersecting the axial direction of the elongated main body with a simple structure.

The light irradiation device of the present disclosure is a light irradiation device for medical use that has an elongated shape and emits light from a most distal end of the light irradiation device. The light irradiation device includes an optical fiber that transmits light emitted by a light source to a tip portion. The tip portion of the optical fiber is formed in a bent portion that is bent with respect to an axial direction of a base portion to which the tip portion is connected. A most distal end of the bent portion in the optical fiber serves as the most distal end of the light emitting device from which light is emitted. The light irradiation device emits light in a direction intersecting the axial direction by emitting the light from the most distal end of the bent portion in the optical fiber.

According to the light irradiation device in the present disclosure, light is directly emitted from the most distal end of the bent portion of the optical fiber in a direction intersecting the axial direction of the base portion. Therefore, the configuration of the tip portion of the light irradiation device is prevented from being complicated, while light emission in a direction intersecting the axial direction can be performed. Furthermore, since the light directly exits the light irradiation device from the most distal end of the bent portion of the optical fiber, light energy loss is less likely to occur as compared to a case where a resin body or the like is used to adjust the light emission direction. Therefore, the light can be efficiently emitted in a direction intersecting the axial direction of the main body of the light irradiation device having an elongated shape with a simple configuration.

It should be noted that the number of optical fibers included in the light irradiation device may be one or more. When a plurality of optical fibers are used, the tip portions of the plurality of optical fibers are formed as the bent portion, so that light is appropriately emitted in a direction intersecting the axial direction of the main body of the light irradiation device.

Furthermore, when a plurality of optical fibers are used, at least one of the optical fibers may be used as an aiming light transmission portion that transmits an aiming light for determining the aiming position for the light irradiation. In this case, by checking the position where the aiming light is emitted, a medical health worker can appropriately determine the irradiation position of the light for treatment.

The entire tip portion of the light irradiation device, together with the tip portion of the optical fiber, may be bent in the axial direction. In this case, by recognizing the bending direction of the tip portion of the light irradiation device, the medical staff can properly know the emitting direction of the light. Therefore, the accuracy of treatment can be further improved.

However, only the tip portion of the optical fiber in the light irradiation device may be bent without bending the tip portion of the light irradiation device. Even in this case, the light can be efficiently emitted in a direction intersecting the axial direction of the main body of the light irradiation device having an elongated shape with a simple configuration.

A bent-portion marker having radiation opacity may be disposed in at least a portion of the bent portion of the tip portion of the light irradiation device. In this case, a health care worker (e.g., a doctor, etc.) can properly recognize the position and the bending direction of the tip portion (i.e., the direction in which the light is emitted) by checking the bent portion marker that appears in the captured image while imaging the inside of a living body using radiation (e.g., X-rays, etc.) and irradiating a living tissue with the light by the light irradiation device 2. Thus, the accuracy of treatment can be further improved.

The most distal end of the bent portion of the optical fiber may be cut at an angle so that the cut surface faces away from the axis of the base portion of the optical fiber. In this case, the cross-sectional area of the cut surface of the core of the optical fiber is enlarged compared to the cut surface that is cut in a direction perpendicular to the axis. Therefore, even if an optical fiber having a large core diameter is not used, the sufficient cross-sectional area of the core from which light is emitted can be sufficiently obtained. Therefore, the light irradiation device can be miniaturized.

The light irradiation density at the time of the light exiting the light irradiation device from the tip end of the optical fiber may be 100 $W/cm^2$ or more and 10,000 $W/cm^2$ or less. In this case, treatment effects by irradiating the light-sensitive substance with the light can easily be obtained appropriately.

Note that the light irradiation density at the time of the light exiting the light irradiation device is more preferably 500 $W/cm^2$ or more and 5,000 $W/cm^2$ or less, and more preferably 800 $W/cm^2$ or more and 2,000 $W/cm^2$ or less. As an example, in the present disclosure, the light irradiation density at the time of the light exiting the light irradiation device is approximately 1,273 $W/cm^2$. Moreover, the above-mentioned condition for the light irradiation density is applicable regardless of the number of optical fibers in the light irradiation device. For example, in a case where light is simultaneously emitted from a plurality of optical fibers and the emitted light is multiplexed, the condition of the light irradiation density of the multiplexed light may be the above condition.

The light irradiation device may further include a stiffening portion that increases stiffness of at least a portion of an area where the bent portion is located. By providing the stiffness portion, it is possible to stabilize the angle of the bent portion with respect to the axial direction of the base portion of the optical fiber, for example. Furthermore, when the bent portion is rotated or pushed, the stiffening portion reduces the possibility of an unintended change in angle of the bent portion or the like. Thus, the accuracy of treatment can be further improved.

The stiffening portion may include a tip stiffening portion that covers at least the most distal end of the bent portion and is made of a material that transmits light emitted from the most distal end of the bent portion. In this case, the stiffness of the tip end of the bent portion is increased by the tip stiffening portion, and light emitted from the most distal end of the bent portion passes through the tip stiffening portion to reach the living tissue. Therefore, the operability of the bent portion, such as the rotating operation and the pushing operation, is easily improved.

The stiffening portion may include a base-end stiffening portion that is disposed in the bent portion at a position closer to the base portion than the most distal end. In this case, the possibility of unintended angle changes or the like occurring on a side of the bent portion closer to the base portion than the most distal end of the bent portion is appropriately reduced. Thus, the accuracy of treatment can be further improved.

The material of the base-end stiffening portion is not necessarily a material having optical transparency. Therefore, many materials can be used for the base-end stiffening portion. For example, the base-end stiffening portion may be made of a material (such as a metal) having a stiffness higher than that of the tip stiffening portion. In this case, the tip stiffening portion obtains both light transmission and stiffening properties, while the base-end stiffening portion further reduces the possibility of angle changes in the bent portion, etc. Thus, treatment can be performed more appropriately.

The light irradiation device further includes a magnetic member that is configured to guide a position or an orientation of the bent portion in a living body using a magnetic force generated by the magnetic member placed in a magnetic field. In this case, while the light irradiation device is inserted into a living body, at least one of the position and orientation of the bent portion of the light irradiation device is appropriately guided. Thus, treatment can be performed more appropriately.

In addition, a light emitting element may be disposed in the tip portion of the light irradiation device to indicate the position of the bent portion by the light emitted using wireless power transfer technology. At least a portion of the light emitting element may be formed of a magnetic member. In this case, not only the position and the orientation of the bent portion of the light irradiation device can be indicated by the light emitting member that emits light, but it is also possible to guide at least one of the position and the orientation of the bent portion by generating magnetic force in the light emitting member. Also, the magnetic member can also be used as the stiffening portion described above. In this case, multiple useful functions are added to the light irradiation device without increasing the number of members.

A light irradiation system in the present disclosure includes a catheter and a light irradiation device. The catheter is formed in an elongated tubular shape and has flexibility. The light irradiation device has an elongated shape, is inserted into a lumen of the catheter, having a most distal end from which light is emitted. The light irradiation device includes an optical fiber that transmits light emitted by a light source to a tip portion. The tip portion of the optical fiber is formed in a bent portion that is bent with respect to an axial direction of a base portion to which the tip portion is connected. A most distal end of the bent portion in the optical fiber serves as the most distal end of the light emitting device from which light is emitted. The light irradiation system emits light in a direction (i.e., a tip direction) intersecting the axial direction by emitting the light from the most distal end of the bent portion in the optical fiber.

According to the light irradiation system in the present disclosure, light is directly emitted from the most distal end of the bent portion of the optical fiber in a direction intersecting the axial direction of the base portion. Therefore, the configuration of the tip portion of the light irradiation device is prevented from being complicated, while light emission in a direction intersecting the axial direction can be performed. Furthermore, since the light directly exits the light irradiation device from the most distal end of the bent portion of the optical fiber, light energy loss is less likely to occur as compared to a case where a resin body or the like is used to adjust the light emission direction. Therefore, the light can be efficiently emitted in a direction intersecting the axial direction of the main body of the light irradiation device having an elongated shape with a simple configuration. Note that at least one of the multiple configurations of the light irradiation device described above can be used for the configuration of the light irradiation device used in the light irradiation system.

A posture holding member may be disposed on an inner circumferential surface of the catheter having a long tubular shape. The posture holding member protrudes inward from the inner circumferential surface of the catheter, thereby coming into contact with the bent portion of the light irradiation device that is pushed into the lumen of the catheter to hold the position of the bent portion. In this case, the bent portion of the light irradiation device comes into contact with the posture holding member, so that the bent portion is held at an appropriate position and angle in the catheter. Therefore, the light emitted from the most distal end of the bent portion can be more accurately emitted to the target site in the living tissue. Thus, the accuracy of treatment can be further improved.

The surface of the posture holding member facing the base portion may diagonally extends toward the base portion from the inner circumferential surface of the catheter. In this case, by coming into contact with the surface of the posture holding member facing the base portion, the bent portion is appropriately angled with respect to the axial direction of the base portion of the optical fiber. Therefore, it is possible to appropriately emit light in a direction intersecting the axial direction.

The catheter may have a protruding marker having radiopaque properties in at least a portion of the posture holding member. In this case, a health care worker (for example, a doctor, etc.) can appropriately recognize the position of the posture holding member with which the bent portion of the light irradiation device is in contact by checking the positions of the protruding marker appearing in the image when irradiating a living tissue with the laser light while imaging the inside of the living body using radiation (for example, X-rays, etc.). Thus, the accuracy of treatment can be further improved.

When the catheter is viewed in the axial direction, a plurality of posture holding members may be disposed at a plurality of positions on the inner circumferential surface of the catheter at a plurality of positions that are offset from each other in the circumferential direction. In this case, a medical health worker can easily and accurately adjust the light irradiating direction by (i) selecting one of the multiple posture holding members, which are located at different position in a circumferential direction from each other and (ii) having the bent portion of the light irradiation device coming into contact with the selected posture holding member. Thus, the accuracy of treatment can be further improved.

A plurality of posture holding members may be disposed at a plurality of positions spaced away from each other in the axial direction of the catheter. In this case, a medical health worker can recognize the position of the target posture holding member in the axial direction, and then push the bent portion of the light irradiation device in the axial direction, thereby easily bringing the bent portion into contact with the target posture holding member.

The details of the method for arranging the multiple posture holding members can be appropriately selected. For example, a plurality of posture holding members may be arranged in a spiral shape on the inner circumferential surface of the catheter having an elongated tubular shape. In this case, a medical health worker can more easily select the target posture holding member with which the bent portion is to come into contact among from the plurality of posture holding members. It is also possible to align the positions of the multiple posture holding members in the axial direction. It may be also possible to use only one posture holding member on the inner circumferential surface of the catheter.

The length of each of the plurality of posture holding members from the inner circumferential surface of the catheter to a tip end thereof may be equal to or less than ½ of the inner diameter of the catheter. In this case, when a medical heath worker brings the bent portion into contact with one of the posture holding members that is located closer to the tip in the axial direction than a particular posture holding member, a medical health worker can push the light irradiation device toward the tip side while avoiding the bent portion coming into contact with the particular posture holding member. Therefore, the operability during insertion of the light irradiation device into the catheter can be improved.

The light irradiation system further includes a light detection transmission member that is configured to transmit light having entered the tip portion of the catheter or the light irradiation device to an optical sensor, or an optical sensor that is disposed in the tip portion. In this case, the state of the light having entering the tip portion of the light irradiation system is appropriately detected by the optical sensor. When the light detection transmission member that transmits light having entered the tip portion to the optical sensor is provided, the state of the light in the tip portion can be appropriately detected without having the configuration of the tip portion of the light irradiation device complicated. Furthermore, when the optical sensor is disposed in the tip portion of the catheter or the light irradiation device, the state of light in the tip portion is directly detected by the optical sensor in the tip portion. In other words, certain changes in the light that may occur during the light transmission process are unlikely to occur. Thus, the state of the light can be detected more accurately and easily.

Note that other sensors may be provided in the tip portion of the light irradiation device separately from or together with the light sensor. For example, a temperature sensor may be disposed near the tip portion of the catheter. In this case, a temperature near the tip portion of the catheter can be appropriately detected. Therefore, for example, an increase in temperature caused by the light being emitted can be appropriately detected.

The catheter may include a plurality of temperature sensors. Each of the plurality of the temperature measurement positions of the plurality of temperature sensors may be arranged in a respective one of the plurality of portions in the catheter. In this case, useful information can be acquired based on temperature detection results at each of the plurality of measurement positions. For example, it is also possible to confirm the direction in which the light is emitted by the light irradiation device by confirming which of the plurality of measurement positions has a higher temperature than other measurement positions. Also, a health care worker can improve treatment accuracy by accurately acquiring the temperature at each measurement position.

The catheter may include a wire that extends from a base side of the catheter to the tip side. At least one of the wires may be arranged spirally in the catheter. Since the wire is arranged in a spiral shape, the rigidity of the catheter having an elongated shape can be appropriately secured as compared to a situation where the wire is arranged to linearly extend along the axial direction. Thus, the accuracy of treatment can be further improved.

Note that the wire arranged in a spiral shape can be appropriately selected. For example, a wire of the temperature sensor (for example, thermocouples, etc.) may be arranged in a spiral shape. Also, when measurement positions (measurement points) of a plurality of temperature sensors are set in the catheter, the measurement positions of the temperature sensors may be respectively arranged at the multiple positions of the spirally arranged multiple wire. In this case, the measurement positions of the plurality of temperature sensors can be easily and appropriately arranged in the axial direction and the circumferential direction of the catheter having an elongated shape.

Also, at least one of the wires may include a material having radiation opacity. In this case, the position of the catheter can be easily recognized appropriately by radiographic imaging. Note, when the wire having irradiation opacity is arranged in a spiral shape, the position of the catheter can be easily recognized.

A portion of the catheter that transmits light from the most distal end of the light irradiation device may be made of a material having a thermal conductivity of 0.1 W/m*K or more. In this case, for example, the tip portion of the light irradiation device can be effectively cooled by blood flow or physiological saline. Accordingly, it is possible to reduce the possibility of various problems occurring due to heat generated by emitting the light. As a result, treatment can be performed more appropriately.

The catheter may further include a catheter tip end fixed to a tip portion. A through hole in the catheter tip end that penetrates axially through the catheter may be formed to have a diameter smaller than the diameter of the light irradiation device. At least a portion of the catheter tip end may be made of a material having radiation opacity. In this case, a medical health care worker (for example, a doctor, etc.) can appropriately adjust the catheter to an appropriate position by recognizing the position of the tip end appearing in the radiographic image. Thus, the accuracy of treatment can be further improved. It should be noted that even if a marker having radiation opacity is provided in the tip portion of the catheter in addition to the catheter tip end, it would be easy to recognize the position of the tip portion of the catheter.

The light source may emit light with a wavelength of 300 nm or more and 2000 nm or less. More preferably, the light source may emit the laser light with a wavelength of 600 nm or more and 1,000 nm or less. In this case, the light irradiation device in the present embodiment is used for treatment for a disease using a light-sensitive substance, making it easier to obtain an appropriate therapeutic effect.

A cooling fluid may flow into the lumen of the catheter after the light irradiation device was inserted into the catheter. In this case, defects (e.g., thermal damage to a living tissue) due to a temperature increase by the light irradiation are appropriately suppressed by the cooling fluid.

Hereinafter, a plurality of typical embodiments according to the present disclosure will be described with reference to the drawings. The light irradiation system 1 in this embodiment is used by being inserted into a lumen of a living body (for example, at least one of a blood vessel, a lymph node, a urethra, a respiratory tract, a digestive organ, a secretory gland, and a reproductive organ). The light irradiation system 1 emits light (laser light in this embodiment) to biological tissue while being inserted into a lumen of a living body. The light irradiation system may be used for at least any therapy such as PDT (photodynamic therapy) and NIR-PIT (Near-Infrared Photoimmunotherapy).

The light irradiation system 1 in the present embodiment includes a light irradiation device 2 and a catheter 3. When the light irradiation system 1 is used, the catheter 3 is inserted into a body lumen first. Next, the light irradiation device 2 is inserted into the lumen 311 of the catheter 3 which has a long tubular shape. After the insertion is complete, the light irradiation device 2 irradiates the biological tissue with light. However, it is also possible to use only the light irradiating device 2 alone without using the catheter 3.

XY axes orthogonal to each other are shown in FIG. 1 to FIG. 3, FIG. 5, FIG. 7 and FIG. 8. In these drawings, the lower side of the drawing (+X direction) is a "tip side," the upper side of the drawing (-X direction) is a "base side," the left side of the drawing (+Y direction) is a "left side," and the right side of the drawing (-Y direction) is a "right side". The light irradiation system 1, the light irradiation device 2, and the catheter 3 are inserted into a living body lumen from the tip side of them. The base side of the system 1 is operated by a health care worker (for example, a doctor, etc.).

(Light Irradiation Device)

Figure 2:
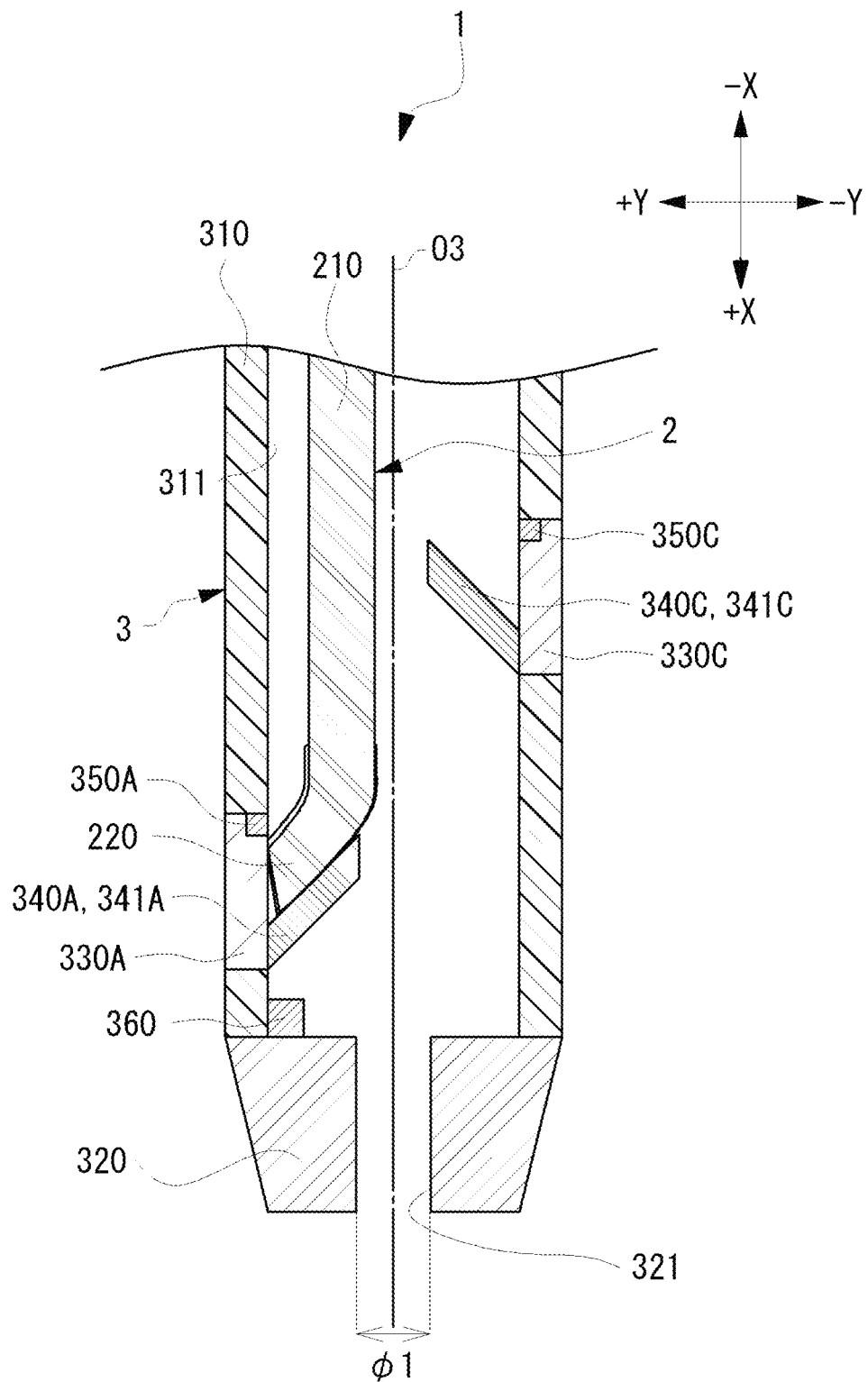
FIG. 2 is an enlarged longitudinal cross-sectional view of the tip portion of the light irradiation system 1 where the light irradiation device is attached to the catheter 3 (a used state).
Figure 3:
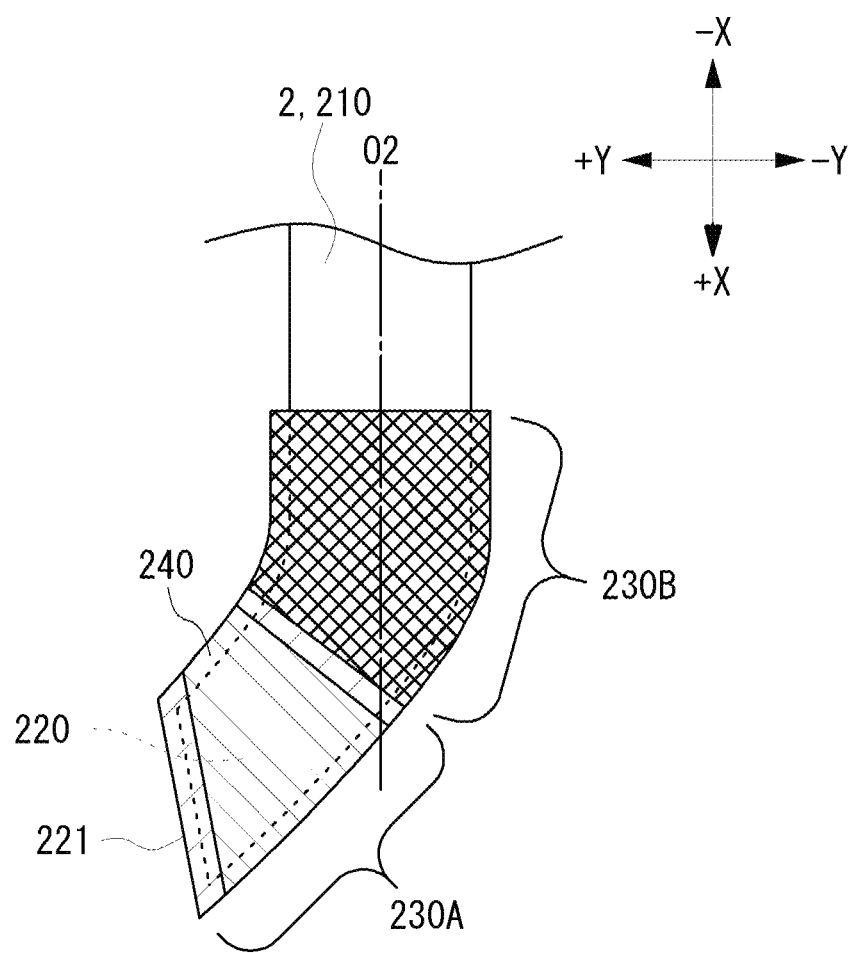
FIG. 3 is an enlarged view of the tip portion of the light irradiation device 2.

Refer to FIGS. 1 to 3, the light irradiation device 2 in this embodiment will be described. The light irradiation device emits light from its most distal end. As shown in FIG. 1, the light irradiation device 2 has an elongated shape. The light irradiation device 2 includes a connector 201 and an optical fiber 210. The connector 201 is located on the base side of the light irradiation device 2 and is held by an operator. The connector 201 includes a pair of blades 202 and a connecting portion 203. The connecting portion 203 has a substantially cylindrical shape. The blades 202 are connected to a base portion of the connecting portion 203. The optical fiber 210 is connected to the inside of the connecting portion 203. Note that the blades 202 and the connecting portion 203 may be integrally formed.

The base portion of the optical fiber 210 is connected via a connector (not shown) to a laser light generating device (light source) 5 that generates laser light either directly or indirectly via another optical fiber. The tip portion of the optical fiber 210 is cut and the cladding and coating are removed. As a result, the light generated by the laser light generating device 5 is transmitted to the tip portion via the optical fiber 210 and is emitted from a core at the center of the tip portion.

More detail, the optical fiber 210 in this embodiment includes a first optical fiber having a tip portion from which light is emitted and a second optical fiber that is connected to the base side of the first optical fiber via a connector. The minimum numerical aperture of the first optical fiber is greater than the maximum numerical aperture of the second optical fiber. As a result, loss during transmission of the light through the optical fiber 210 is reduced overall.

The first optical fiber includes a first core extending in a longitudinal direction (i.e., a direction of the axis O2) of the light irradiation device 2, and a first cladding covering an outer circumferential surface (i.e., an outer surface) of the first core. The first core is disposed approximately at the center of the first cladding, and has a higher optical refractive index than the first cladding. The first cladding has a uniform refractive index. The first optical fiber transmits light by total reflection utilizing the difference in refractive index between the first core and the first cladding. The first optical fiber in this embodiment is a plastic optical fiber in which the first core and the first cladding are both made of resin. The first core can be made of, for example, at least one of polymethylmethacrylate (PMMA), polystyrene, polycarbonate, deuterated polymer, norbornene-based polymer, and the like. As the first optical fiber, instead of a plastic optical fiber, other optical fibers (for example, a silica glass optical fiber, a multi-component glass optical fiber, etc.) may be used.

The second optical fiber is connected to the base side of the first optical fiber. The second optical fiber includes a second core and a second cladding covering an outer circumferential surface (i.e., an outer surface) of the second core. The second optical fiber in this embodiment is a silica glass optical fiber in which the second core and the second cladding are both made of silica (silicon dioxide). The second core 260c can be made, for example, using silicon dioxide as a main component and germanium dioxide, fluorine, or the like as additives. The second cladding 260cl can be made of, for example, pure silica glass. For the second optical fiber 260, a plastic optical fiber or a multi-component glass optical fiber may be used instead of the silica glass optical fiber.

The laser light generating device 5 may emit laser light with a wavelength of 300 nm or more and 2000 nm or less. More preferably, the laser light generating device 5 may emit the laser light with a wavelength of 600 nm or more and 1000 nm or less. In this case, the light irradiation device 2 is used for a treatment for a disease using a light-sensitive substance, making it easier to obtain an appropriate therapeutic effect. Note that in this embodiment, the center wavelength of the laser light emitted by the laser light generating device 5 is approximately 690 nm.

Referring to FIGS. 2 and 3, the configuration of a tip portion of the light irradiation device 2 in this embodiment is explained. FIG. 2 is an enlarged longitudinal cross-sectional view of the tip portion of the light irradiation system 1 where the light irradiation device 2 is attached to (inserted into) the catheter 3 (a used state). FIG. 3 is an enlarged view of the tip portion of the light irradiation device 2. As shown in FIG. 3, the tip portion of the optical fiber is formed in a bent portion 220 that is bent with respect to the direction of the axis O2 of the base portion to which the tip portion is connected. The light irradiation device 2 emits light from a most distal end 221 of the bent portion 220 in the optical fiber 210, thereby emitting light in a direction intersecting the direction of the axis O2 of the base portion (in this embodiment, a direction obliquely intersecting the axis O2). In other words, the most distal end 221 of the bent portion 220 serves as the most distal end of the light irradiation device 2 from which light is emitted. The bent portion 220 may emit light in a direction perpendicular to the direction of the axis O2 of the base end.

According to the light irradiation device 2 in this embodiment, light is directly emitted from the most distal end 221 of the bent portion 220 of the optical fiber 210 in a direction intersecting the direction of the axis O2 of the base portion. Therefore, the configuration of the tip portion of the light irradiation device 2 is prevented from being complicated, while light emission in a direction intersecting the direction of the axis O2 is performed. Furthermore, since light directly exits the light irradiation device 2 from the most distal end 221 of the bent portion 220 of the optical fiber 210, light energy loss is less likely to occur as compared to a case where a resin body or the like is used to adjust the direction of emitting light. Therefore, the light can be efficiently emitted in a direction intersecting the direction of the axis O2 of the main body of the light irradiation device 2 having an elongated shape with a simple structure.

As shown in FIGS. 2 and 3, in this embodiment, the entire tip portion of the light irradiation device 2 is bent with respect to the direction of the axis O2 so that the tip portion of the optical fiber 210 is bent. Therefore, by recognizing the bending direction of the tip portion of the light irradiation device 2, a medical health worker can properly recognize the emitting direction of the light. Thus, the accuracy of treatment can be further improved.

As shown in FIG. 3, at least a part of the bent portion 220 in the optical fiber 210 of the light irradiation device 2 includes a bent portion marker 240 having radiation opacity. Therefore, a health care worker (e.g., a surgeon, etc.) can properly recognize the position and the bending direction of the bent portion 220 (i.e., the direction in which the light is emitted) by checking the bent portion marker 240 that appears in the captured image while imaging the inside of a living body using radiation (e.g., X-rays, etc.) and irradiating a living tissue with the light by the light irradiation device 2. Thus, the accuracy of treatment can be further improved.

As shown in FIGS. 2 and 3, the tip of the bent portion 220 of the optical fiber 210 is obliquely cut so that the cut surface (the most distal end 221) faces away from the axis O2 (see FIG. 3) of the base portion of the optical fiber 210. As a result, the cross-sectional area of the cut surface of the core of the optical fiber 210 is enlarged compared to the cut surface that is cut in a direction perpendicular to the axis O2. Therefore, even if an optical fiber having a large core diameter is not used, the sufficient cross-sectional area of the core from which light is emitted can be sufficiently obtained. Therefore, the light irradiation device 2 can be miniaturized.

As shown in FIG. 3, at least a part of the optical fiber 210 where the bent portion 220 is located includes stiffening portions 230 (230A, 230B) for increasing stiffness of the optical fiber 210. By providing the stiffening portions 230, it is possible to stabilize the angle of the bent portion 220 with respect to the direction of the axis O2 of the base portion of the optical fiber 210, for example. Furthermore, when the bent portion 220 is rotated or pushed, the stiffening portions 230 reduce the possibility of an unintended change in angle of the bent portion 220 or the like. Thus, the accuracy of treatment can be further improved.

In particular, the stiffening portions 230 includes a tip stiffening portion 230A. The tip stiffening portion 230A covers at least the tip end of the bent portion 220 with a material that transmits light emitted from the most distal end 221 of the bent portion 220. As a result, the rigidity of the tip end of the bent portion 220 is increased by the tip stiffening portion 230A, and light emitted from the most distal end 221 of the bent portion 220 passes through the tip stiffening portion 230A and is emitted onto a living tissue. Therefore, the operability of the bent portion 220, such as the rotating operation and the pushing operation, is easily improved.

Further, the stiffening portions 230 includes a base-end stiffening portion 230B. The base-end stiffening portion 230B increases the stiffness of the optical fiber 210 by covering the base side of the bent portion 220 rather than the tip end (in this embodiment, the connecting portion between the bent portion 220 and the base portion to which the bent portion 220 is connected). Therefore, the possibility of unintended angle changes or the like occurring on a side of the bent portion 220 close to the base side than the tip end of the bent portion is appropriately reduced. Thus, the accuracy of treatment can be further improved. The material of the base-end stiffening portion 230B is not necessarily a material having optical transparency. Therefore, many materials can be used for the base-end stiffening portion 230B. As one example, the base-end stiffening portion 230B in this embodiment is made of a material (in this embodiment, woven metal) having a stiffness higher than that of the tip stiffening portion 230A. Therefore, the tip stiffening portion 230A achieves both light transmission and stiffening properties to the optical fiber 210, while the base-end stiffening portion 230B further reduces the possibility of change in the angle of the bent portion 220. Thus, treatment can be performed more appropriately.

As shown in FIG. 3, a magnetic member 240 is disposed in the bent portion 220 of the optical fiber 210. The magnetic member 240 serves as a guide member to guide at least one of a position and an orientation (a direction) of the bent portion in a lumen of a living body by a magnetic force generated by the magnetic member placed in a magnetic field. Accordingly, when the light irradiation device 2 is inserted into a living body, at least one of the position and direction of the bent portion 220 of the light irradiation device 2 is appropriately guided. In detail, in this embodiment, the magnetic member 240 is disposed in the bent portion 220 so that the orientation of the most distal end 221 of the bent portion 220 is appropriately guided by the magnetic member. Therefore, the emitting direction of the light is appropriately controlled. In this embodiment, the bent portion marker 240 also serves as the magnetic member 240. However, the bend portion marker and the magnetic member may be provided separately.

In addition, a light emitting element may be disposed in the tip portion of the light irradiation device 2 to indicate the position of the bent portion 220 by the light emitting element emitting light using wireless power transfer technology. For example, at least a portion of the light emitting element may be formed of the magnetic member 240. In this case, not only the position and the orientation of the bent portion 220 of the light irradiation device is indicated by the light emitting member that emits light, but it is also possible to guide at least one of the position and the orientation of the bent portion 220 by generating magnetic force in the light emitting member. Also, the magnetic member can also be used as the stiffening portion described above. In this case, multiple useful functions are added to the light irradiation device 2 without increasing the number of members.

The light irradiation density at the time of light emitting the light irradiation device 2 from the most distal end of the optical fiber 210 (that is, the most distal end 221 of the bent portion 220) is set to 100 W/cm$^2$ or more and 10,000 W/cm$^2$ or less. In this case, treatment effects by irradiating the light-sensitive substance with the light can be obtained appropriately. Note that the light irradiation density at the time of the laser light exiting the light irradiation device 2 is more preferably 500 W/cm$^2$ or more and 5,000 W/cm$^2$ or less, and more preferably 800 W/cm$^2$ or more and 2,000 W/cm$^2$ or less. As an example, in this embodiment, the light irradiation density at the time of the laser light exiting the light irradiation device 2 is approximately 1,273 W/cm$^2$.

(Catheter)

The catheter 3 in this embodiment will be described with reference to FIGS. 1, 2, 4, and 5. As shown in FIG. 1, the catheter 3 has an elongated tubular shape. The catheter 3 includes a connector 301, a shaft 310, and a tip end 320. The connector 301 is located on a base side of the catheter 3 and is held by an operator (i.e., a surgeon). The connector 301 includes a pair of blades 302 and a connecting portion 303. The connecting portion 303 has a substantially cylindrical shape. The blades 302 are connected to a base portion of the connecting portion 303. The shaft 310 is connected to a tip portion of the connecting portion 303. Note that the blades 302 and the connecting portion 303 may be integrally formed.

The shaft 310 is preferably antithrombotic, flexible, and biocompatible. At least one of a resin material and a metal material, etc., may be used as a material for the shaft 310. For example, a polyamide resin, a polyolefin resin, a polyester resin, a polyurethane resin, a silicon resin, or the like may be used as a resin material. As a metal material, a stainless steel such as SUS 304, a nickel-titanium alloy, a cobalt-chromium alloy, a tungsten steel, etc., may be used. Note, the shaft 310 may be made by combining multiple materials.

The shaft 310 has an elongated tubular shape extending along an axis O3. The shaft 310 in this embodiment is formed in a hollow cylinder shape with both the tip and base ends being open. The lumen 311 in the shaft 310 serves as a guide wire lumen for inserting a guide wire into the catheter 3 during delivery of the catheter 3. The lumen 311 serves as a device lumen for inserting the light irradiation device 2 into the catheter 3 after the delivery of the catheter 3.

As shown in FIGS. 1 and 2, the tip end 320 is connected to the tip portion of the shaft 310. The tip end 320 has an outer shape that tapers in diameter from the base side to the tip side in order for the catheter 3 to advance smoothly into a biological lumen. A through hole 321 passing through the tip end 320 in a direction of the axis O2 is formed approximately at the center of the tip end 320. As shown in FIG. 3, the inner diameter Φ1 of the through hole 321 is smaller than the inner diameter Φ3 of the lumen 311 of the shaft 310 and smaller than the outer diameter of the bent portion 220 of the optical fiber 210 of the light irradiation device 2. Therefore, even if the light irradiation device 2 is sufficiently pushed forward into the lumen 311 of the catheter 3, the optical fiber 210 of the light irradiation device 2 is unlikely to protrude through the through hole 321.

Figure 4:
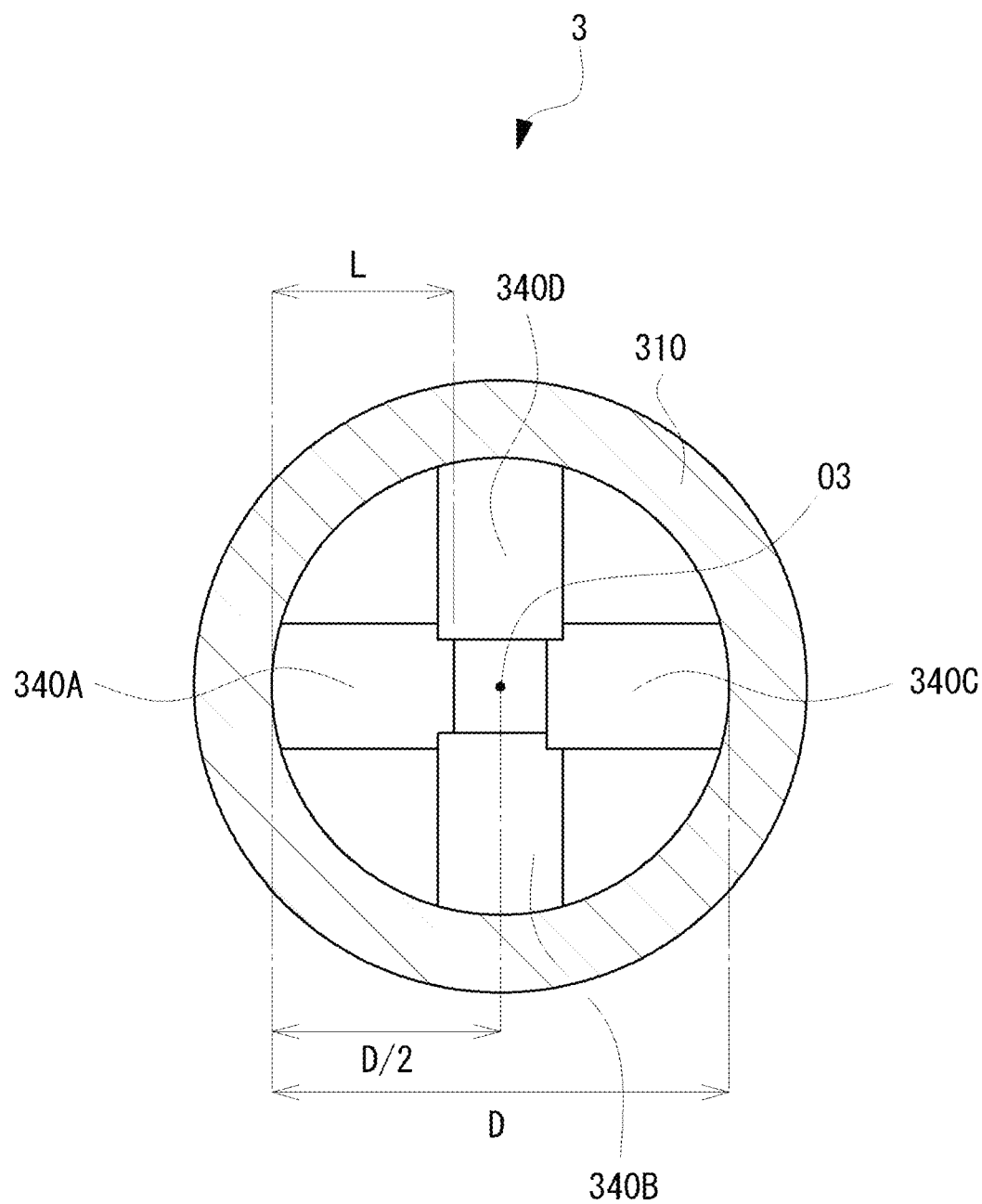
FIG. 4 shows the shaft 310 of the catheter 3 as viewed from the base end side along the axis O3.
Figure 5:
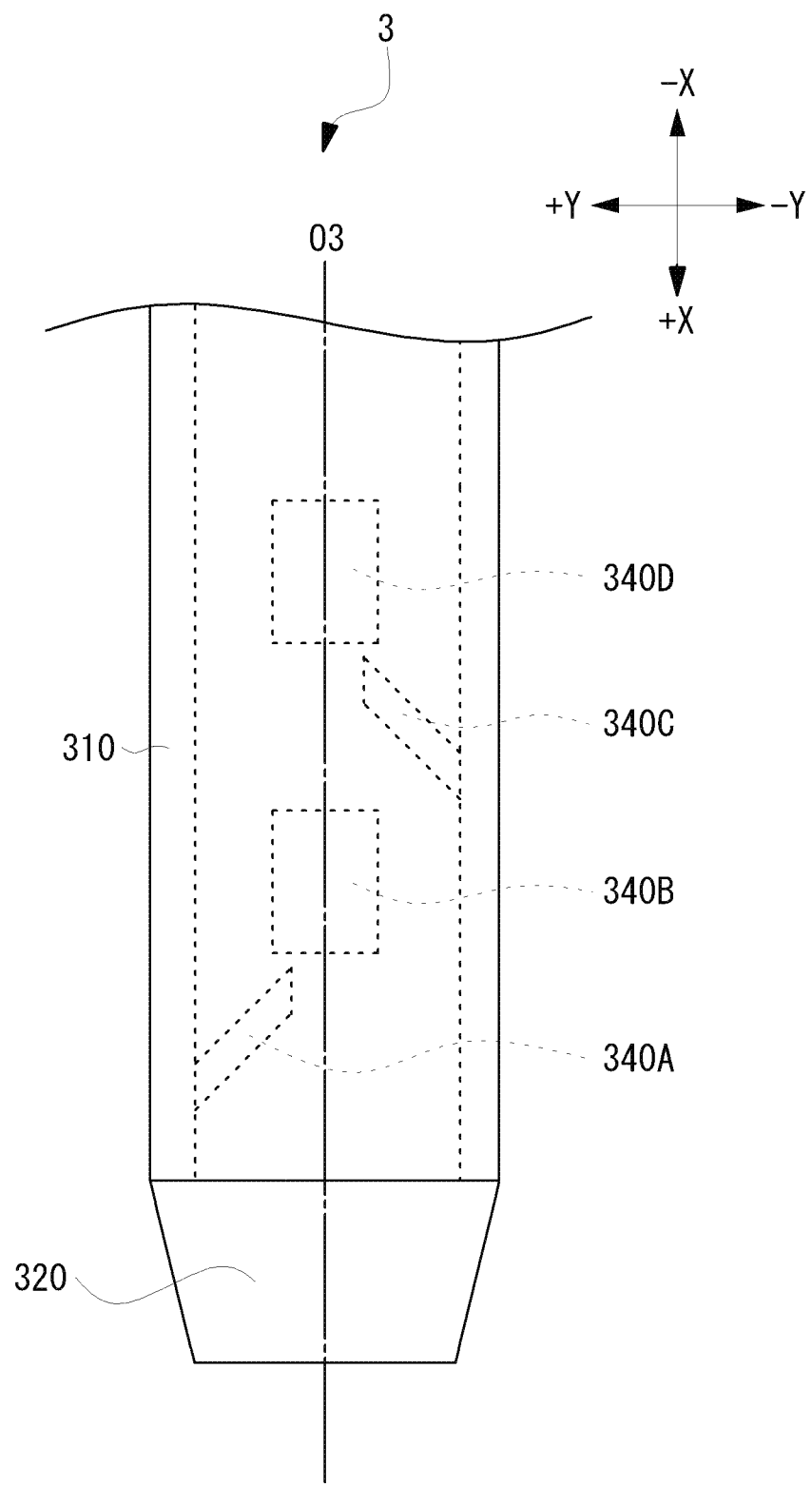
FIG. 5 is a diagram showing the positions of a plurality of posture holding members 340 disposed in the catheter 3 by dotted lines.

As shown in FIGS. 2, 4, and 5, the inner surface (i.e., the lumen 311) of the shaft 310 of the catheter 3 includes posture holding members 340 (340A, 340B, 340C, 340D) that maintain the posture of the bent portion 220 of the light irradiation device 2. Each of the posture holding members 340 protrudes inward (i.e., toward the axis O3) from the inner circumferential surface of the shaft 310 of the catheter 3, whereby the bent portion 220 of the light irradiation device 2 comes into contact with one of the posture holding members 340. As a result, the bent portion 220 is maintained at an appropriate position and angle in the catheter 3. Therefore, the light emitted from the most distal end 221 of the bent portion 220 can be more accurately emitted to the target site in the living tissue. Thus, the accuracy of treatment can be further improved.

As shown in FIG. 2, the surface of the posture holding member 340 facing the base side (i.e., the surface facing upward, which is the −X direction in FIG. 2) is angled toward the base side from the inner circumferential surface of the shaft 310 of the catheter 3 to the inside of the shaft 310 (i.e., approaches the axis O3). Although the details will be described later, the bent portion 220 of the light irradiation device 2 is pushed forward into the shaft 310 from the base side toward the tip side. Therefore, by coming into contact with the surface of the posture holding member 340 facing the base side, the angle of the bent portion 220 is more easily held with respect to the direction of the axis O2 (see FIG. 3) of the base portion of the optical fiber 210. Therefore, it is possible to appropriately emit light in a direction intersecting the axis O2.

At least a part of each of the posture holding members 340 (in this embodiment, the entire posture holding members 340) includes a radiopaque protruding marker 341. (In FIG. 3, only the protruding marker 341A disposed in the posture holding member 340A and the protruding marker 341C disposed in the posture holding member 340C are illustrated.) When the light irradiation device 2 irradiates a biological tissue with laser light while imaging the inside of the living body using radiation (e.g., X-rays, etc.), a medical health worker can appropriately recognize the position of the posture holding member 340 with which the bent portion 220 of the light irradiation device 2 is in contact by checking the position of the protruding marker 341 that appears in the captured image. Thus, the accuracy of treatment can be further improved.

FIG. 4 shows the shaft 310 of the catheter 3 as viewed from the base side along the axis O3. As shown in FIG. 4, when the catheter 3 is viewed in the direction of the axis O3, multiple posture holding members 340A, 340B, 340C, and 340D are disposed at multiple positions on the inner surface of the shaft 310 of the catheter 3 (i.e., the lumen 311) that have different circumferential angles (i.e., at different positions). A medical health worker can easily and accurately adjust the light irradiating direction by (i) selecting one of the multiple posture holding members 340A, 340B, 340C, and 340D, which are located at different position in a circumferential direction from each other, and (ii) having the bent portion 220 of the light irradiation device 2 coming into contact with the selected posture holding member that is oriented in the direction in which the medical health worker wants to emit the light. Thus, the accuracy of treatment can be further improved.

As shown in FIGS. 4 and 5, the multiple posture holding members 340A, 340B, 340C, and 340D are disposed at multiple positions spaced away from each other in the direction of the axis O3 of the catheter 3. Therefore, a medical health worker can recognize the position of the target posture holding member in the direction of the axis O3, and then push the bent portion 220 of the light irradiation device 2 in the direction of the axis O3, thereby easily bringing the bent portion 220 into contact with the target posture holding member.

In detail, in this embodiment, a plurality of posture holding members 340A, 340B, 340C, and 340D are spirally arranged on the inner circumferential surface of the shaft 310 of the catheter 3 having an elongated tubular shape. Therefore, a medical health worker can more easily select the target posture holding member with which the bent portion 220 is to come into contact among from the plurality of posture holding members 340A, 340B, 340C, and 340D.

As shown in FIG. 4, the length L of each of the multiple posture holding members 340A, 340B, 340C, and 340D from the inner circumferential surface of the shaft 310 of the catheter 3 to an inner end is less than or equal to ½ of the inner diameter D of the shaft 310 of the catheter 3. Therefore, when a medical heath worker brings the bent portion 220 into contact with one of the posture holding members that is located closer to the tip side in the direction of the axis O3 than a particular posture holding member, the medical health worker can push the bent portion 220 of the light irradiation device 2 toward the tip side while avoiding the bent portion 220 coming into contact with the posture holding member that is located closer to the medical health worker than the target posture holding member. Therefore, the operability during insertion of the light irradiation device 2 into the catheter 3 can be improved.

As shown in FIG. 4, light transmission portions 330 that transmit the light emitted from the most distal end 221 of the bent portion 220 are formed on a tip side surface (a part of a side surface of the tip side in this embodiment) of the shaft 310 in the catheter 3. In this embodiment, each of the light transmission portions 330 is disposed at a position at which the bent portion 220 is held by the corresponding posture holding member 340 (in FIG. 4, only the light transmission portion 330A adjacent to the posture holding member 340A and the light transmission portion 330C adjacent to the posture holding member 340C are illustrated.). Therefore, the light irradiation system 1 in this embodiment can locally irradiate a particular site (location) of a living body by transmitting the light emitted from the most distal end 221 of the bent portion 220 of the light irradiation device 2 in a direction intersecting the axis O3.

In this embodiment, the portion of the shaft 310 of the catheter 3 where the bent portion 220 is held by the posture holding member 340 is partially made of a material that transmits light to serve the light transmission portion 330. However, it is also possible to change the configuration of the light transmission portion. For example, the light transmission portion may be formed in the catheter by making the entire shaft 310 or the entire tip portion of the shaft 310 with a material that transmits light.

A portion of the catheter that transmits light from the most distal end 221 of the light irradiation device 2 is made of a material having a thermal conductivity of 0.1 W/m*K or more. Therefore, for example, the tip portion of the light irradiation device 2 can be effectively cooled by blood flow or physiological saline. Accordingly, it is possible to reduce the possibility of various problems occurring due to heat generated by emitting the light. As a result, treatment can be performed more appropriately.

As shown in FIG. 4, an optical sensor 350 is disposed in the tip portion of the shaft 310 of the catheter 3. Thus, the state of light in the tip portion of the catheter 3 is directly detected by the optical sensor 350 at the tip portion. In other words, changes in the characteristics of light that may occur during the transmission process are unlikely to occur in light detected by the optical sensor 350. Thus, the state of the light can be detected more accurately and easily. In this embodiment, in order to detect light emitted from the tip end of the bent portion 220 that is held by one of the plurality of posture holding members 340A, 340B, 340C, and 340D, a plurality of optical sensors 350 are disposed in positions close to the plurality of corresponding posture holding members 340A, 340B, 340C, and 340D. (In FIG. 4, only the optical sensor 350A close to the posture holding member 340A and the optical sensor 350C close to the posture holding member 340C are shown.) Therefore, when the bent portion 220 is held by any one of the posture holding members, the state of light is appropriately detected by the corresponding optical sensor. Note, in order to simplify the illustration, the wire extending from the optical sensor 350 is not illustrated.

As shown in FIG. 4, the catheter 3 in this embodiment includes a temperature sensor 360 in the tip portion. Therefore, for example, an increase in temperature caused by the light being emitted to a living tissue can be appropriately detected.

In this embodiment, at least a part of the tip end 320 provided at the tip portion of the shaft 310 of the catheter 3 (the entire tip end 320 in this embodiment) is made of a material having radiation opacity to serve as a marker. Therefore, the position of the tip portion of the catheter 3 can be properly recognized by a radiographic image or the like.

(Usage)

One example of usage of the light irradiation system 1 in this embodiment is described. First, an operator inserts a guide wire (not shown) into a biological lumen. Next, the operator inserts the guide wire from the through hole 321 of the tip end 320 of the catheter 3 into the lumen 311, and then pulls out the guide wire from the base side of the connector 301. The operator pushes the catheter 3 into the biological lumen along the guide wire and moves at least one of the multiple light transmission portions 330 disposed in the catheter 3 to the target site for light irradiation. It should be noted that, when moving the catheter 3 within the biological lumen, the operator can appropriately move the catheter 3 to the target site by confirming the positions of the protruding markers 341 shown in the radiographic images. The operator then removes the guide wire from the catheter 3.

Next, the operator inserts the light irradiation device 2 from the base side opening of the connector 301 of the catheter 3, and pushes the light irradiation device 2 into the lumen 311 of the catheter 3 in the biological lumen. The operator brings the bent portion 220 indicated by the bent portion marker 240 into contact with a target posture holding member 340 among the plurality of posture holding members 340 indicated by the protruding markers 341. As a result, the posture of the bent portion 220 of the optical fiber 210 in the light irradiation device 2 is appropriately held by the target posture holding member 340. In this state, light is generated from the laser light generating device 5, and the light is locally emitted from the tip portion of the bent portion 220 to the target site.

The operator puts cooling fluid into the lumen 311 of the catheter 3 after the light irradiation device 2 was inserted into the catheter 3. In this case, defects (e.g., thermal damage to a living tissue) due to a temperature increase by the light irradiation are appropriately suppressed by the cooling fluid.

Modification

Figure 6:
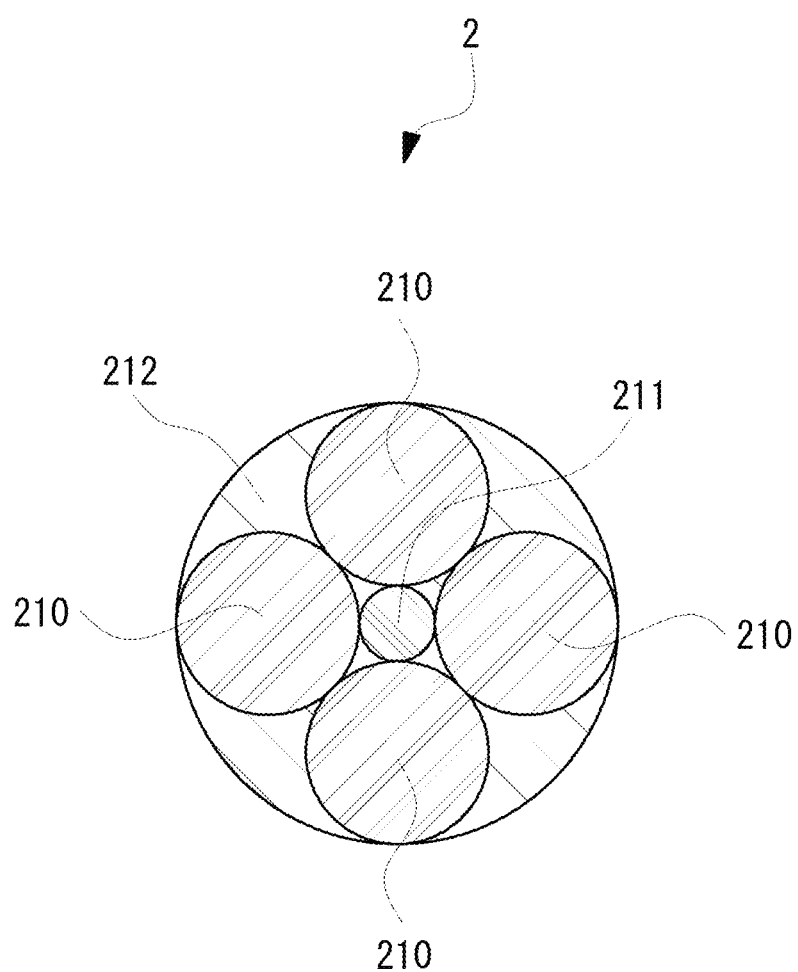
FIG. 6 is a cross-sectional view of a device body 212 of a light irradiation device 2 according to a first modification.
Figure 7:
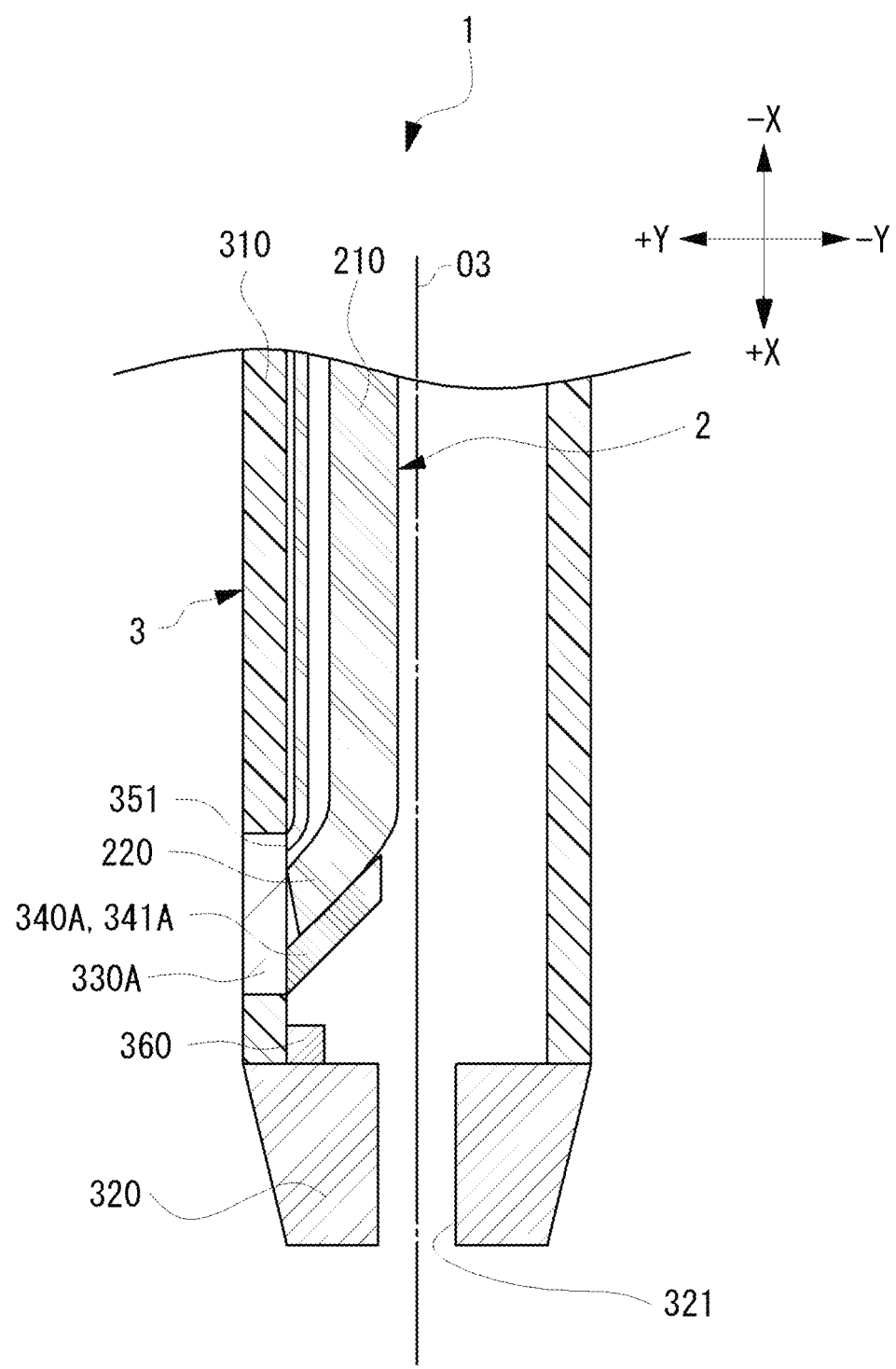
FIG. 7 is an enlarged longitudinal cross-section around the tip portion of the light irradiation system 1 according to a second modification.
Figure 8:
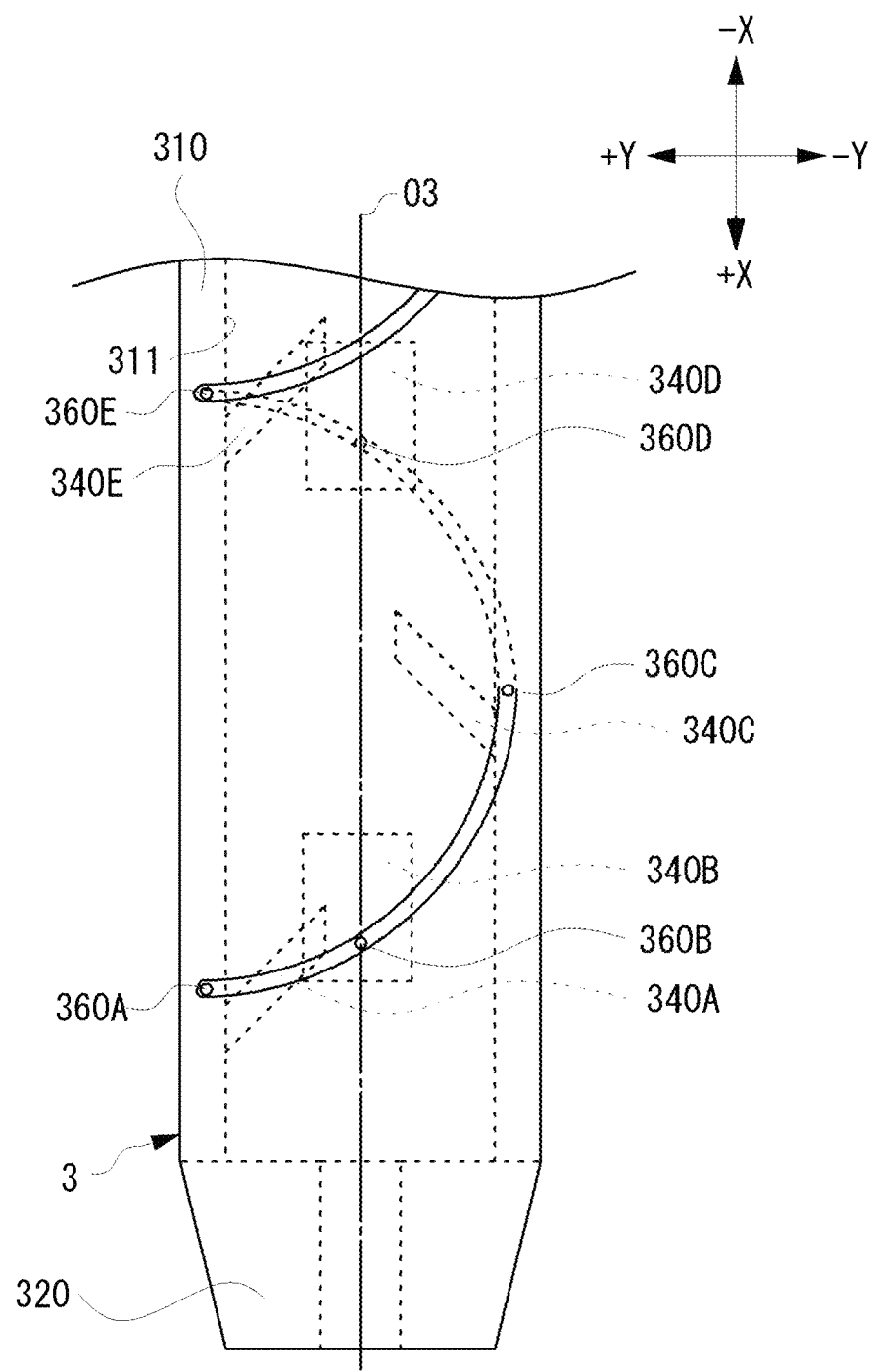
FIG. 8 is an enlarged view of a portion near the tip portion of a catheter 3 according to a third modification.

The technology disclosed in the above embodiments is only one example. Accordingly, it is also possible to change the technology exemplified in the above embodiments. Referring to FIGS. 6 to 8, modifications to the above embodiments will be described. Note, it is possible to adopt a configuration similar to the embodiment described above for a part of each of a first modification shown in FIG. 6, a second modification shown in FIG. 7, and a third modification shown in FIG. 8. Accordingly, among the configurations of the first to third modifications, parts that can adopt a configuration similar to the embodiment described above are given the same number as the above embodiment, and the description is omitted or simplified.

FIG. 6 is a cross-sectional view of a device body 212 of a light irradiation device 2 according to a first modification. The device body 212 of the light irradiation device 2 in the first modification includes a plurality of optical fibers 210 therein. Although not illustrated in detail, in the tip portion of the device body having the plurality of optical fibers 210, a bent portion (similar to the above embodiment) is formed by bending the plurality of optical fibers 210 collectively. As described above, the number of optical fibers 210 included in the light irradiation device 2 may be one or more.

Furthermore, the optical fibers provided in the device body 212 in the first modification include an aiming optical fiber 211 that transmits aiming light for determining an aiming position (an aiming spot) for the light irradiation. Therefore, by checking the position where the aiming light reaches, a medical health worker can appropriately set the irradiating position of the light for treatment. In the example shown in FIG. 6, the aiming optical fiber 211 is disposed at the center of the plurality of optical fibers 210 that emit light for treatment. Thus, a medical health worker can more accurately aim the light for treatment using the aiming light.

FIG. 7 is an enlarged longitudinal cross-section around the tip portion of the light irradiation system 1 according to a second modification. The catheter 3 in the second modification is provided with a light detection transmission member 351 that transmits light having entered the tip portion (near the position where light exits the bent portion 220 of the light irradiation device 2 in this modification) to an optical sensor (not shown). The light detection transmission member 351 in this embodiment is an optical fiber, which is inserted from a part of the shaft 310 of the catheter 3 into the shaft 310 toward the base side and is connected to an optical sensor. In the second modification, the state of the light at the tip portion is appropriately detected while avoiding complication of the configuration of the tip portion of the catheter 3 due to the light sensor. Furthermore, as shown in the second modification, the number of posture holding members 340 provided in the catheter 3 may be one.

FIG. 8 is an enlarged view of a portion near the tip portion of a catheter 3 according to a third modification. A catheter 3 according to the third modification includes multiple temperature sensors 360 (360A, 360B, 360C, 360D, 360E). The measurement positions (the measurement points indicated by 360A, 360B, 360C, 360D, and 360E in this modification) of the plurality of temperature sensors 360 are respectively arranged in a plurality of portions of the tip portion of the catheter 3. In detail, in the example shown in FIG. 8, the measurement positions of the multiple temperature sensors 360 are disposed near positions at which light passes through guided by the multiple posture holding members 340 (340A, 340B, 340C, 340D, 340E). Thus, useful information can be acquired based on temperature detection results at each of the plurality of measurement positions. For example, it is also possible to confirm the direction in which the light is emitted by confirming which of the plurality of measurement positions has a higher temperature than other measurement positions. Also, a health care worker can improve treatment accuracy by accurately acquiring the temperature at each measurement position.

In the catheter 3 of the third modification, the wire of the temperature sensors 360 is arranged spirally in the shaft 310 of the catheter 3. Thus, the rigidity of the catheter 3 having an elongated shape can be appropriately secured as compared to the wire that linearly extends along the axial direction. Thus, the accuracy of treatment can be further improved. As one example, in this modification, an elongated thermocouple with multiple measurement points is used as the temperature sensors 360. By arranging the wire of the elongated temperature sensors 360 in a spiral shape, the rigidity of the catheter 3 is secured.

In the catheter 3 of the third modification, the wire of the temperature sensors 360 includes a material having radiation opacity. Thus, the position of the catheter 3 can be easily recognized appropriately by radiographic imaging. Note, in the third modification, the wire of the temperature sensors 360 having radiation opacity extends in a spiral shape, making it easier to recognize the position of the catheter 3.

It is also possible to adopt only some of the configurations exemplified in the embodiment and the modifications described above in a light irradiation system, light irradiation device, or catheter. Also, it is possible to combine multiple configurations shown in the embodiment and the modifications. As described above, it is also possible to independently use only the light irradiation device 2 without using the catheter 3.

The invention claimed is:

1. A light irradiation device for medical use that has an elongated shape and is configured to emit light from a most distal end after the light irradiation device was inserted into a lumen of a living body, the light irradiation device comprising:
an optical fiber that is configured to transmit light emitted by a light source to a tip portion of the optical fiber, wherein
the tip portion of the optical fiber is formed in a bent portion that is bent with respect to an axial direction of a base portion to which the tip portion is connected,
a most distal end of the bent portion has a cut surface facing in a tip direction to serve as a most distal end surface of the light irradiation device from which light is emitted,
light having exited the most distal end surface is emitted in the tip direction of the bent portion to an outside of the light irradiation device by emitting the light from the most distal end surface of the bent portion in the optical fiber,
the tip direction is a direction intersecting the axial direction of the base portion,
the optical fiber includes a stiffening portion in at least a portion of an area where the bent portion is located,
the stiffening portion is fixed to the bent portion of the optical fiber while allowing the light to be emitted in the tip direction from the most distal end surface of the bent portion, and
an angle of the bent portion with respect to the axial direction of the base portion of the optical fiber is stabilized by increasing a stiffness of the area in the optical fiber where the stiffening portion is disposed as compared to the optical fiber without the stiffening portion.

2. The light irradiation device according to claim 1, wherein
the tip portion of the optical fiber is bent by entirely bending a tip portion of the light irradiation device.

3. The light irradiation device according to claim 2, wherein
a bent-portion marker having radiation opacity is disposed at at least a portion of the bent portion in the irradiation device.

4. The light irradiation device according to claim 1, wherein
the most distal end of the bent portion of the optical fiber is diagonally cut to have the cut surface facing in a direction away from an axis of the base portion.

5. The light irradiation device according to claim 1, wherein
the light has a light irradiation density of 100 W/cm$^2$ or more and 10,000 W/cm$^2$ or less at a time of the light exiting the light irradiation device from a tip end of the optical fiber.

6. The light irradiation device according to claim 1, wherein
the stiffening portion includes a tip stiffening portion that is made of a material that transmits light emitted from the most distal end of the bent portion, and
the tip stiffening portion is configured to cover at least the most distal end of the bent portion.

7. The light irradiation device according to claim 1, wherein
the stiffening portion includes a base-end stiffening portion that is disposed in the bent portion at a position closer to the base portion than the most distal end.

8. The light irradiation device according to claim 1, further comprising
a magnetic member that is configured to guide at least one of a position or an orientation of the bent portion within a living body using a magnetic force generated by the magnetic member placed in a magnetic field.

9. A light irradiation system for medical use that is used after the light irradiation system was inserted into a lumen of a living body, comprising:
a catheter that is formed in an elongated tubular shape; and
a light irradiation device that is formed in an elongated shape, the light irradiation device being inserted into a lumen of the catheter and having a most distal end from which light is emitted, wherein
the light irradiation device includes an optical fiber that transmits light emitted by a light source to a tip portion of the optical fiber,
the tip portion of the optical fiber is formed in a bent portion that is bent with respect to an axial direction of a base portion to which the tip portion is connected,
a most distal end of the bent portion has a cut surface facing in a tip direction to serve as a most distal end surface of the light irradiation device from which light is emitted,
light having exited the most distal end surface is emitted in the tip direction of the bent portion to an outside of the light irradiation device by emitting the light from the most distal end surface of the bent portion in the optical fiber,
the tip direction is a direction intersecting the axial direction of the base portion,
the optical fiber includes a stiffening portion in at least a portion of an area where the bent portion is located,
the stiffening portion is fixed to the bent portion of the optical fiber while allowing the light to be emitted in the tip direction from the most distal end surface of the bent portion, and
an angle of the bent portion with respect to the axial direction of the base portion of the optical fiber is stabilized by increasing a stiffness of the area in the optical fiber where the stiffening portion is disposed as compared to the optical fiber without the stiffening portion.

10. The light irradiation system according to claim 9, wherein
the catheter includes a posture holding member that protrudes from an inner circumferential surface of the catheter, and
the posture holding member is configured to hold a posture of the bent portion when the bent portion of the light irradiation device that is pushed into a lumen of the catheter is in contact with the posture holding member.

11. The light irradiation system according to claim 10, wherein
the posture holding member has a surface facing in a direction to a base portion of the catheter, and
the surface of the posture holding member diagonally extends from the inner circumferential surface of the catheter toward the base portion of the catheter.

12. The light irradiation system according to claim 10, wherein a protruding marker having radiation opacity is disposed in at least a portion of the posture holding member.

13. The light irradiation system according to claim 10, wherein
the posture holding member are a plurality of posture holding members, and
the plurality of posture holding members are arranged on the inner circumferential surface of the catheter to be circumferentially offset from each other when viewed in the axial direction of the catheter.

14. The light irradiation system according to claim 13, wherein
the plurality of posture holding members are separated away from each other in the axial direction of the catheter.

15. The light irradiation system according to claim 14, wherein
each of the plurality of posture holding members has a length from the inner circumferential surface of the catheter to an inner edge of each of the plurality of posture holding members, and
the length is less than or equal to ½ of an inner diameter of the catheter.

16. The light irradiation system according to claim 9, further comprising
a light detection transmission member that is configured to transmit light having entering a tip portion of the catheter or the light irradiation device to an optical sensor; or
an optical sensor that is disposed in the tip portion.

17. The light irradiation system according to claim 9, wherein
the catheter further includes a plurality of temperature sensors, and
a plurality of temperature measurement positions of the plurality of temperature sensors are located in a plurality of portions of the catheter.

18. The light irradiation system according to claim 9, wherein
the catheter further includes a wire that extends from a base side of the catheter to a tip side, and
the wire extends in a spiral shape.

19. The light irradiation system according to claim 9, wherein
at least a portion of the catheter that transmits light from the most distal end of the light irradiation device is made of a material having a thermal conductivity of 0.1 W/m*K or more.

* * * * *